US011202902B2

(12) United States Patent
Najar

(10) Patent No.: US 11,202,902 B2
(45) Date of Patent: Dec. 21, 2021

(54) BLOOD PUMP HOUSING DEVICE

(71) Applicant: Scandinavian Real Heart AB, Västerås (SE)

(72) Inventor: Azad Najar, Västerås (SE)

(73) Assignee: SCANDINAVIAN REAL HEART AB, Vasteras (SE)

( * ) Notice: Subject to any disclaimer, the term of this patent is extended or adjusted under 35 U.S.C. 154(b) by 280 days.

(21) Appl. No.: 16/074,964

(22) PCT Filed: Feb. 9, 2017

(86) PCT No.: PCT/EP2017/052837
§ 371 (c)(1),
(2) Date: Aug. 2, 2018

(87) PCT Pub. No.: WO2017/137486
PCT Pub. Date: Aug. 17, 2017

(65) Prior Publication Data
US 2019/0038821 A1 Feb. 7, 2019

(30) Foreign Application Priority Data

Feb. 10, 2016 (SE) .................................. 1650171-0
Dec. 6, 2016 (SE) .................................. 1651606-4

(51) Int. Cl.
*A61M 60/892* (2021.01)
*A61M 60/40* (2021.01)
(Continued)

(52) U.S. Cl.
CPC ........ *A61M 60/892* (2021.01); *A61M 60/122* (2021.01); *A61M 60/258* (2021.01);
(Continued)

(58) Field of Classification Search
CPC .............. A61M 1/1087; A61M 1/1081; A61M 1/1096; A61M 1/12; A61M 1/1086;
(Continued)

(56) References Cited

U.S. PATENT DOCUMENTS 3,608,088 A 9/1971 Dorman et al.
4,863,461 A 9/1989 Jarvik
(Continued)

FOREIGN PATENT DOCUMENTS

WO WO-2016/020219 A1 2/2016

OTHER PUBLICATIONS

International Search Report and Written Opinion dated May 15, 2017 by the International Searching Authority for Application No. PCT/EP2017/052837, which was filed on Feb. 9, 2017, and published as WO 2017/137486 on Aug. 17, 2017 (Invento—Azad Najar; Applicant—Scandinavian Real Heart AB) (9 pages).
(Continued)

*Primary Examiner* — Brian A Dukert
*Assistant Examiner* — Rebecca Lynee Zimmerman
(74) *Attorney, Agent, or Firm* — Ballard Spahr LLP

(57) ABSTRACT

A blood pump housing device designed to enclose and protect a total artificial heart when implanted in a subject is disclosed. The blood pump housing device comprises a first and second artificial heart pump receiving part (3a, 3b) configured to receive and partly enclose a first and a second artificial heart pump (20a, 20b) of a total artificial heart (TAH); and a first and second pump actuation enclosing part (4a, 4b) configured to partly enclose a first and second pump actuation means (60a, 60b), said artificial heart pump receiving parts (3a, 3b) and pump actuation means enclosing parts (4a, 4b) are arranged to connect to each other in a leak-free manner.

16 Claims, 12 Drawing Sheets

(51) Int. Cl.
*A61M 60/50* (2021.01)
*A61M 60/122* (2021.01)
*A61M 60/258* (2021.01)
*A61M 60/857* (2021.01)
*A61M 60/894* (2021.01)
*A61M 60/268* (2021.01)

(52) U.S. Cl.
CPC ............ *A61M 60/40* (2021.01); *A61M 60/50* (2021.01); *A61M 60/857* (2021.01); *A61M 60/894* (2021.01); *A61M 60/268* (2021.01)

(58) Field of Classification Search
CPC .............. A61M 1/1046; A61M 1/1051; A61M 1/1008; A61M 1/1037; A61M 1/1089; A61M 1/098; A61M 60/00–90
See application file for complete search history.

(56) References Cited

U.S. PATENT DOCUMENTS

| | | |
|---|---|---|
| 5,693,091 A | 12/1997 | Larson et al. |
| 2006/0253194 A1 | 11/2006 | Dial |
| 2009/0149950 A1 | 6/2009 | Wampler |
| 2009/0287305 A1* | 11/2009 | Amalaha .................. A61M 1/12 623/3.11 |
| 2012/0130484 A1* | 5/2012 | Shu ..................... A61M 1/1053 623/3.11 |
| 2015/0038772 A1 | 2/2015 | Heilman et al. |

OTHER PUBLICATIONS

International Preliminary Report on Patentability dated Feb. 14, 2018 by the International Searching Authority for Application No. PCT/EP2017/052837, which was filed on Feb. 9, 2017, and published as WO 2017/137486 on Aug. 17, 2017 (Inventor—Azad Najar; Applicant—Scandinavian Real Heart AB) (17 pages).

* cited by examiner

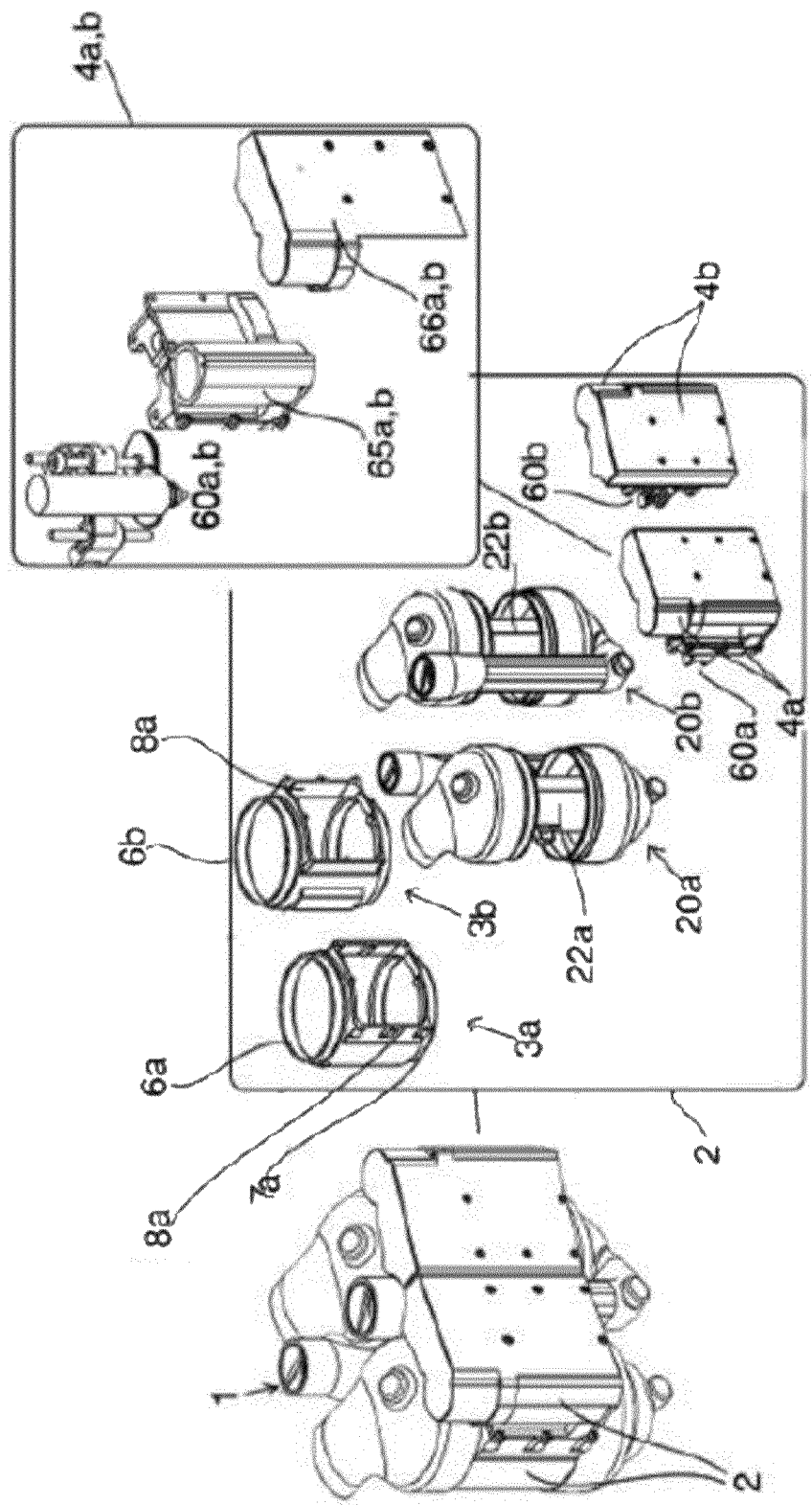

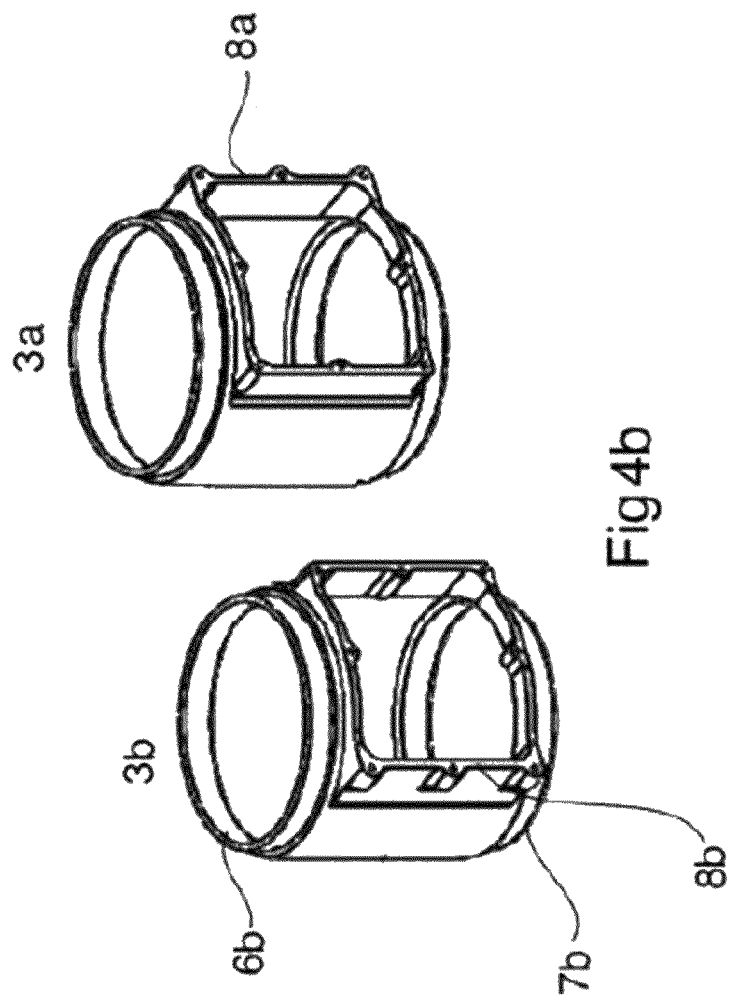
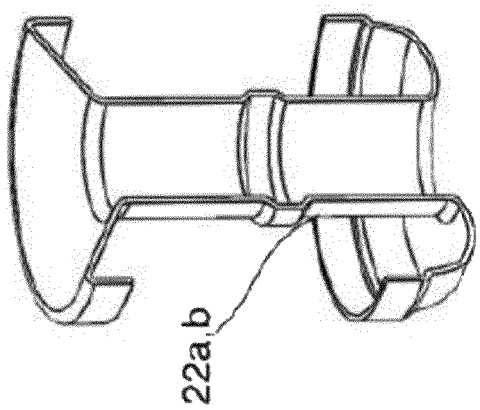

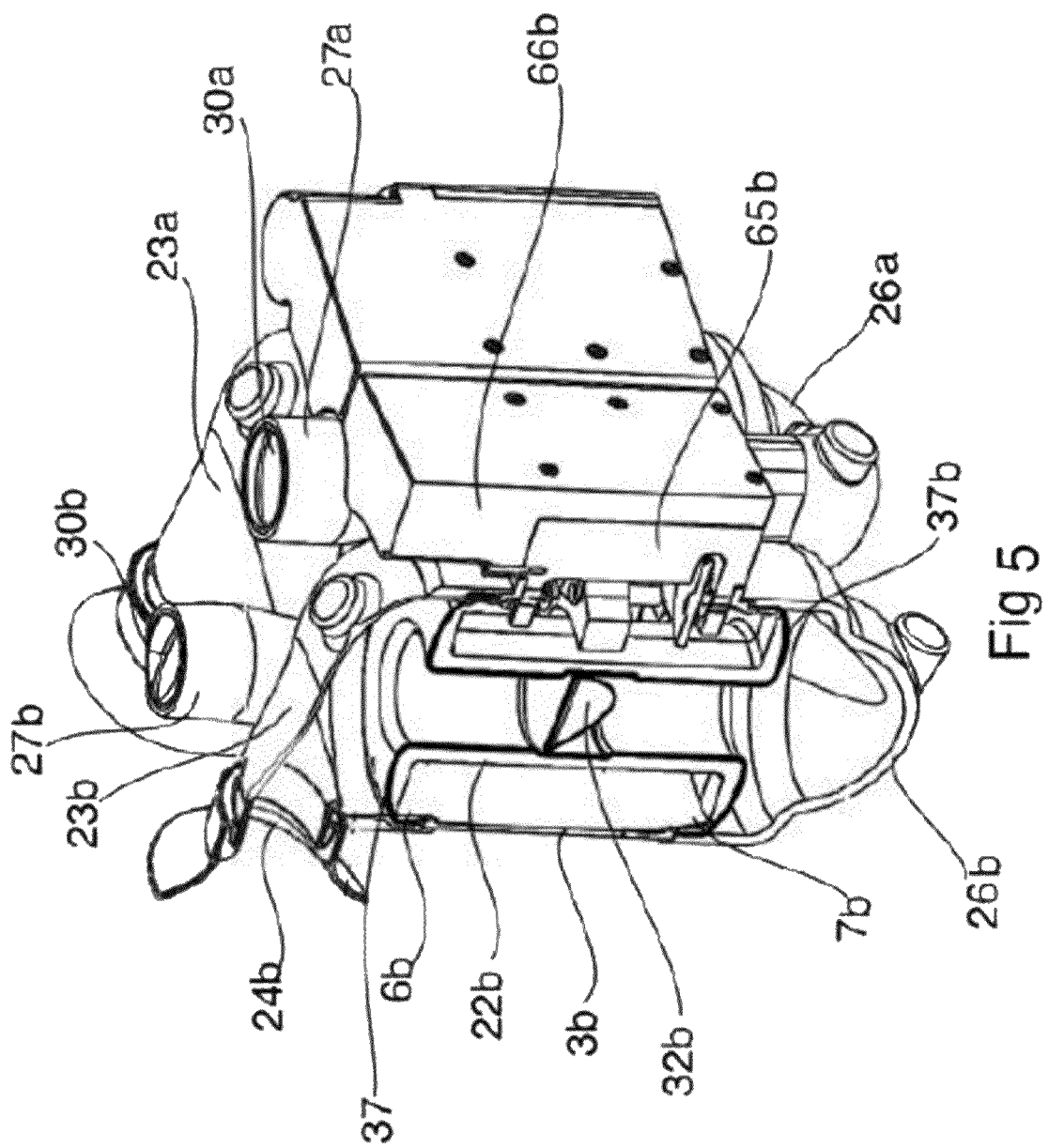

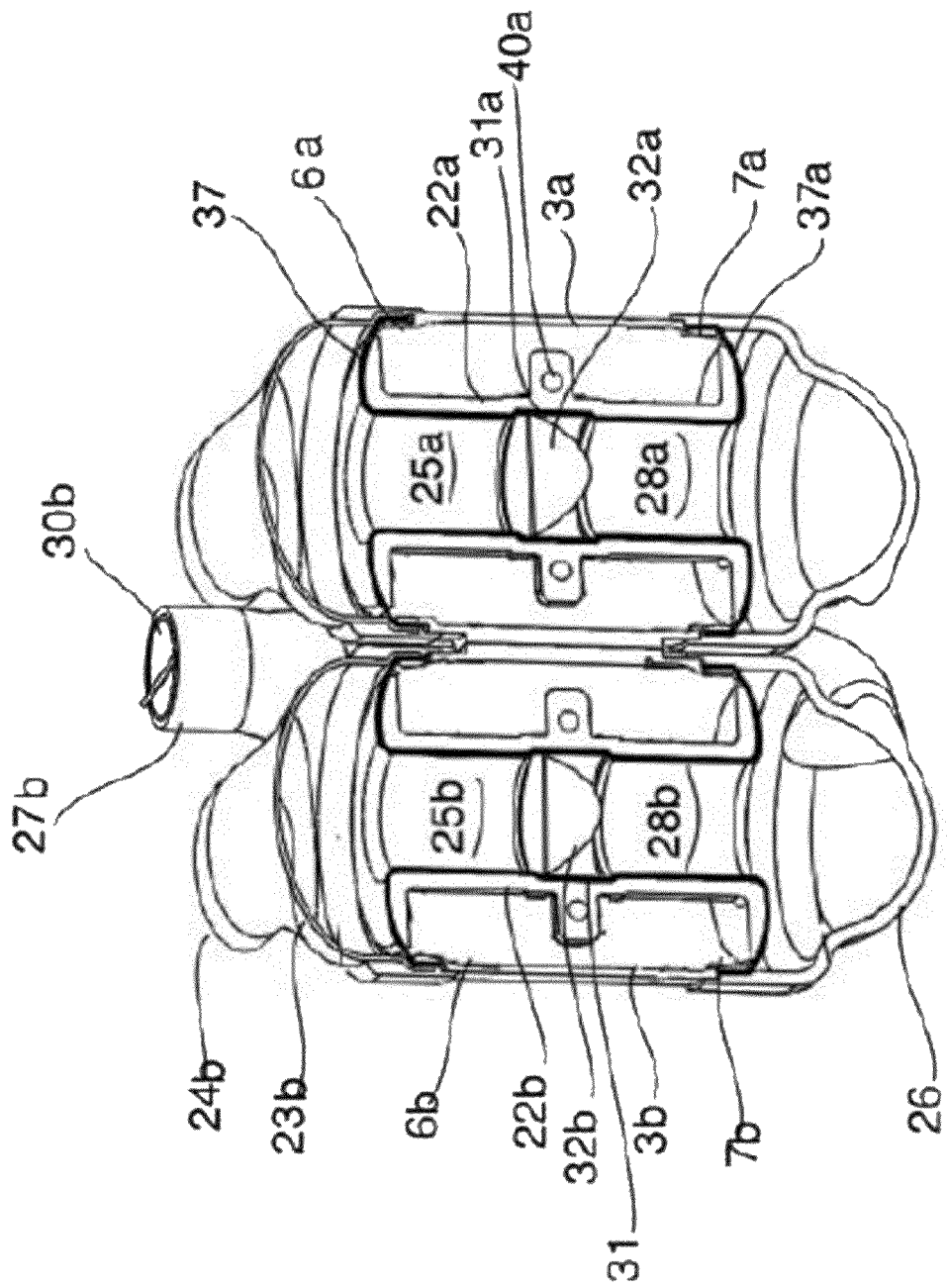

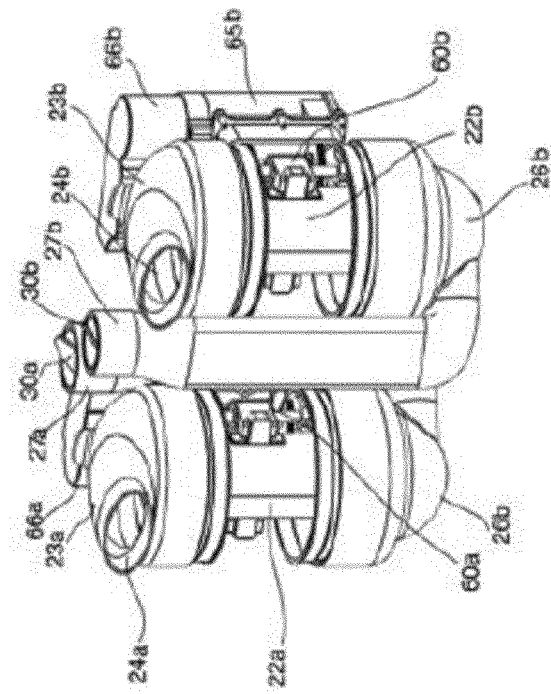
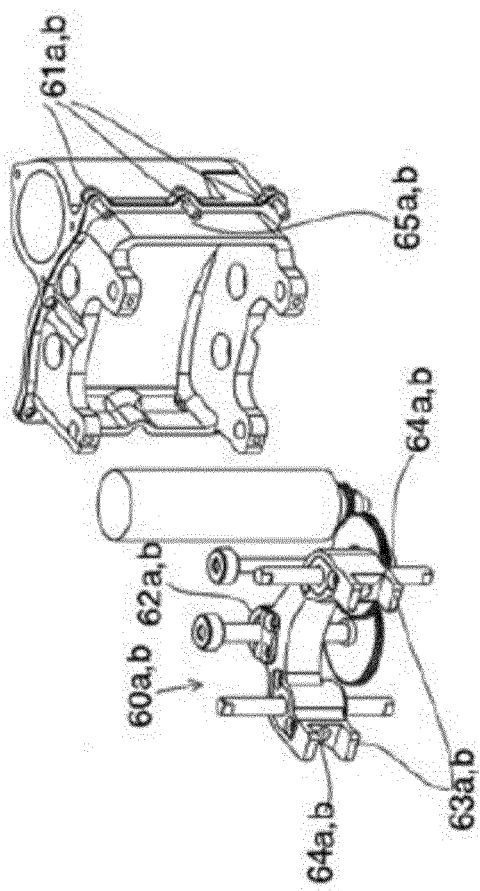
Fig 14b
Fig 14a

BLOOD PUMP HOUSING DEVICE

CROSS-REFERENCE TO RELATED APPLICATIONS

This application is a U.S. National Phase Application of International Application No. PCT/EP2017/052837, filed Feb. 9, 2017, which claims priority to Swedish Patent Application Nos. SE 1650171-0, filed Feb. 10, 2016, and SE 1651606-4, filed Dec. 6, 2016, each of which are hereby incorporated by reference in their entirety.

TECHNICAL FIELD

The present disclosure relates to a blood pump housing device arranged to receive and enclose a Total Artificial Heart (TAH) when implanted inside a subject.

BACKGROUND OF THE INVENTION

The main function of the heart in the human body is to circulate blood through the blood vessels in order to transport oxygen, nutrition, and waste products to and from body cells. Many diseases may affect the heart such as myocardial infarction, hypertension, valve insufficiency and various heart muscle diseases. The end result of such diseases may be heart failure which means that the heart has lost its ability to pump enough blood to the lungs and body tissues.

The symptoms of heart failure are shortness of breath, edema and fatigue. The only treatment option available for a patient suffering from advanced heart failure is heart transplantation. However, due to a lack of sufficient number of donor hearts the majority of advanced heart failure patients die while waiting for a heart transplant operation.

For this reason many efforts have been made during the last 50 years to develop a mechanical heart which can replace a diseased heart entirely. Until now only a few Total Artificial Hearts (TAH) i.e. mechanical hearts/heart prosthesis have been developed which have the capacity to completely replace the diseased heart.

WO2016/020219 discloses a four-chambered TAH which is designed as a human heart. This TAH comprises a first and a second artificial heart pump corresponding to the left and right heart of the natural heart. Each pump comprises a valve cylinder which is divided into two chambers by means of a moving plane comprising a one-way valve which corresponds to the Atrioventricular (AV) plane in a natural heart. Pump actuating means are configured to apply a movement to said valve cylinders in an upward and downward direction in response to control signals from a control unit such that when the valve cylinders move in an upward direction inside the blood pump housing device, the valves provided in the valve planes are in an open position allowing a flow of blood from the artificial atrium into the artificial ventricle, and when the valve cylinders move in a downward direction the valves are in the closed position and blood is ejected from the artificial ventricle and exit therefrom through outlet channels.

When implanted in a subject it is important that the TAH is enclosed in a casing which protects the surrounding tissue from moving parts but it is also important that it prevents entry of body fluids into the TAH. It has therefore been an object of the inventors to provide a blood pump housing device designed to protect both the TAH and the surrounding tissue when implanted in a subject. A further object has been to provide a blood pump housing device which will also facilitate the implantation of the TAH in the subject and any subsequent servicing of the implanted TAH.

SUMMARY OF THE INVENTION

In a first aspect the present invention relates to a blood pump housing device designed to enclose and protect a total artificial heart when implanted in a subject.

The blood pump housing device as disclosed herein is advantageously designed to receive, enclose and protect a four-chambered total artificial heart comprising a first and a second artificial heart pump corresponding to the left and right heart of the natural heart together with a first and second pump actuating means for inducing a blood flow in a body's vascular system.

The blood pump housing device comprises, a first and second artificial heart pump receiving part configured to receive and partly enclose said first and second artificial heart pumps. The blood pump housing device further comprises a first and second pump actuation enclosing part configured to at least partly enclose said first and second pump actuation means. Said first and second pump actuation parts are advantageously connected to said first and second pump enclosing parts in a leak-free manner. Together the four parts form the blood pump housing device.

Separating the blood pump housing device into four parts facilitates the assembly of the four-chambered total artificial heart during manufacture, and especially during implantation of the total artificial heart in a subject. The first and second artificial heart pump receiving parts and the first and second pump actuation enclosing parts may be assembled together by connecting means selected from the group consisting glue, connecting screws, bolts and nuts, clamps and/or clips. The connections between the pump receiving parts and pump actuation enclosing parts must be leak-free in order to prevent entry of body fluids into the artificial heart pump.

The two artificial heart pump receiving parts may be provided as separate units but are advantageously interconnected. Each pump receiving part is configured to receive and enclose a valve cylinder of the artificial heart pump which is movably arranged inside the pump receiving part. The inside of the valve cylinder is separated by a valve plane provided with a valve which is housed inside the valve cylinder. The valve plane is arranged in the valve cylinder, such that the valve plane divides the valve cylinder into two parts, one upper part and one lower part.

Advantageously the first artificial heart pump and the second artificial heart pump are identical and the valves provided in the valve cylinders of each artificial heart pump correspond to the mitral valve on the left side of the natural heart and the tricuspid valve on the right side.

Each pump receiving part has an upper open end and a lower open end. The upper open end is arranged with an upper cover provided with an inlet channel. The upper cover together with the upper part above the valve plane of the valve cylinder forms an artificial atrium corresponding to an atrium of the natural heart. The lower open end of the pump receiving part is arranged with a lower cover provided with an outlet channel, which together with the lower part below the valve plane of the valve cylinder forms an artificial ventricle corresponding to a ventricle of the natural heart. The outlet channels are provided with one-way valves to ensure a unidirectional flow of blood through the artificial heart pumps.

The upper and lower covers are arranged onto the upper and lower open ends of the pump receiving parts in a leak-free manner. Advantageously the upper and lower covers are glued to the upper and lower open ends. Alternatively a gasket made from a biocompatible rubber or silicon material is arranged between the covers and the valve cylinder casings. The upper and lower covers may also be fastened onto the valve cylinder casings by means of connecting screws, bolts and nuts, clamps and/or clips.

The pump receiving parts and the pump actuation enclosing parts of the blood pump housing device are advantageously made from a stiff material, such as e.g. a biocompatible material such as, titanium, ceramics, Polytetrafluoroethylene (PTFE) coated metal, diamond coated metal, silicone or polyurethane coated metals or a combination thereof.

In order for the four-chambered total artificial heart to circulate the blood in a leak-free manner, the inside of the artificial atriums and ventricles are provided with a flexible lining material made from plastic or rubber. The flexible lining may also be comprised of two or more layers of lining material to improve its strength. In case the flexible lining comprises two layers two electrodes could be placed between the first layer and the second layer to send an alarm if the first layer is partially or totally damaged and blood can be detected between these two layers. These two electrodes are advantageously connected to an electronic control unit. The flexible lining material is advantageously made from a biocompatible material like silicone, polyurethane or another biocompatible material.

The flexible lining material is in the artificial atrium connected to an upper cylinder junction arranged between the upper cover and the top edge of the upper open end of the pump receiving part by the use of biocompatible glue or other means to prevent any leakage through the upper cylinder junction. The flexible lining material is also in the artificial ventricle connected to a lower cylinder junction arranged between the lower cover and the bottom edge of the lower open end of the pump receiving part by the use of biocompatible glue or other means to prevent any leakage through the lower cylinder junction.

The outlet channels of the four-chambered total artificial heart are located on the lower covers and provided with one-way outlet valves to prevent the return of blood back into the artificial ventricle after the blood has been ejected through the outlet channel. The outlet channel valves correspond to the aortic valve or the pulmonary valve respectively of the natural heart.

By means of the flexible lining a leak-free pipeline is formed in the artificial heart through which blood is pumped in a continuous pulsating flow from the entrance of the inlet channel through the artificial atrium, the valve, the ventricle and out through the outlet channel.

The TAH further comprises a first and second pump actuation means configured to apply movement to the valve cylinders of the first and second pumps. The pump actuating means are received into and at least partly enclosed by the pump actuation enclosing parts. The pump actuation enclosing parts each comprise pump actuation casing configured to receive and enclose a pump actuating means. Advantageously the two pump actuation casings are interconnected. The pump actuation enclosing parts with the pump actuation casings are configured to dock to docking apertures provided on the first and second pump enclosing parts such that said first and second pump actuating means enclosed therein may apply movement to the valve cylinders of the artificial heart pumps in an upward and downward direction in response to control signals from a control unit.

The pump actuation enclosing parts with pump actuation casings dock to the docking apertures in a leek free manner to prevent body fluids from entering the blood pump housing device. The pump actuation enclosing parts are docked to the docking apertures by means of connecting means selected from the group consisting of glue, connecting screws, bolts and nuts, clamps and/or clips. Advantageously first and second pump actuation casings of the pump actuation enclosing part are connected to the docking apertures in a reversible manner such that the pump actuation enclosing part is easily removed if the pump actuation means requires maintenance. Connecting means such as connecting screws, bolts and nuts, clamps and/or clips facilitate opening and closing of the blood pump housing device and are therefore preferred. Advantageously a gasket is provided in the junction between the first and second pump actuation casings and the docking apertures.

The pump actuating means are configured to apply movement to said valve cylinders in an upward and downward movement inside the pump receiving parts in response to control signals from a control unit. When the valve cylinders move in an upward direction, the valves provided in the valve planes are in an open position allowing a flow of blood from the artificial atrium into the artificial ventricle. When the valve cylinders move in a downward direction the valves are in the closed position and blood is ejected from the artificial ventricles and exit therefrom through the outlet channels. Each artificial heart pump contains a pump actuating means and both the first and the second artificial heart pumps of the heart operate simultaneously and in the same direction.

The upward and downward motion of the valve cylinders may be achieved in many different ways. In one advantageous embodiment the pump actuation means actuates rotation of a series of gears interconnected to a rack and pinion. The pump actuation means is advantageously an electromechanical motor. A plurality of gears of different sizes is configured to interact with one another and an interconnected pinion. Said interconnected gears and pinions translate said rotational movement to a first and second linear toothed means such as e.g. a rack, provided on each side of the valve cylinder. When the pump actuation means rotates the gears and pinions in a first rotational direction, teeth provided on the pinion interact with teeth on a linear toothed gear (i.e. the rack) provided on the each side of the cylinder and causes the linear rack with the valve cylinder to move relative to the pinion in a first linear direction. Thereafter the pump actuation means changes direction into a second rotational direction opposite to said first rotational direction and moves said valve cylinder in a second linear direction opposite to said first linear direction. The rotational speed and length of rotational movement is adjusted to provide appropriate speed and length of the up-and-down movement of the valve cylinders to induce correct blood flow through the TAH and into the vascular system.

In an alternative embodiment the pump actuating means comprises a ball screw or a roller screw which translates a rotational motion provided by a pump actuation means, such as e.g. an electromechanical motor into a linear up-and-down motion of the valve cylinders. Said pump actuation means actuates rotational movement of a plurality of gears which interact with said ball screws/roller screws. Said ball screw/roller screw is interconnected with a semicircular base comprising two projecting arms which partly encircle said valve cylinders. Each valve cylinder is provided with two or more magnets arranged to interact with magnets provided on said encircling arms. When the pump actuation means rotates the gears in a first rotational direction, the ball screw/roller screw moves said base with encircling arms in a first linear direction causing the valve cylinder to move in a first linear direction.

Thereafter the pump actuation means changes direction into a second rotational direction opposite to said first rotational direction and moves said ball screw/roller screw in a second linear direction opposite to said first linear direction thereby moving said valve cylinder in a second linear direction opposite to said first linear direction. The rotational speed and length of rotational movement is adjusted to provide appropriate speed and length of the up-and-down movement of the valve cylinders to induce correct blood flow through the TAH and into the vascular system.

The energy to power the pump actuating means may be supplied by an external source via a cable through the skin, or alternatively by an implanted battery. The implanted battery may be recharged from the outside via a cable or by means of induction or ultra sound.

Advantageously the pump actuation enclosing part may further comprise a separate and detachable power source housing configured to store any power source used to power the pump actuation means such as rechargeable batteries. The power source housing may also house any microcomputers and/or electronic chips used to receive signals from sensors in the artificial four-chambered heart or to control the pump actuation means.

The detachable power source housing may be removed without having to access any other part of the blood pump housing device.

Although technical advancements during the last decade have improved the durability and mechanical stability of heart prostheses, TAHs may require maintenance from time to time. The pump actuation means comprises several moving parts such as motors, electronics, gears and bearings that may have limited useful life. As described above the pump actuation means as well as the power source housing are integrated and together form the pump enclosing part. This design of the blood pump housing device facilitates maintenance of mechanical parts and/or electronic control unit or change of batteries as the pump actuation enclosing part can easily be disassembled from the pump receiving part and exchanged for a new one. There is no need for long and time consuming surgery. The connecting means connecting the pump actuation casings of the pump actuation enclosing part to the docking apertures are easily disassembled, the pump actuation enclosing part comprising the pump actuation means and maybe the power source is removed and exchanged for a new one. The new pump actuation enclosing part is docked to the docking apertures of the pump receiving part and connected thereto by means of connecting means.

For implantation of the four-chambered total artificial heart inside a subject, the surgeon removes the diseased heart but keeps some parts of the right and left atrium walls including the sinus node. The remaining parts of the atriums are sutured to inlet cuffs provided on the inlet channels of the upper covers. A first end of said inlet cuff is advantageously made from a wide strip of vessel graft tissue (e.g. Dacron material). The second end of the inlet cuff is advantageously fitted with a fast connection such as a blocking stripe made from glass fiber reinforced silicone or other material used for this purpose. Alternatively some other fast connection can be used. Said fast connections connect to the inlet channels. Alternatively, collar cuffs may be glued to the inlet channels. The glue should be a biocompatible glue material. The outlet channels of the four-chambered total artificial heart are advantageously connected to the aortic and pulmonary arteries by means of an outlet cuff analogous to the manner described for the inlet channels above.

After having connected the inlet and outlet channels of both the first and second heart pumps to the Patient's atrium and blood vessels, air must be removed from the four-chambered heart system. A de-airing handle may be assembled to the valve cylinder casings of the artificial heart pump receiving part by means of screws. The manual de-airing handle may manually operate the valve cylinder in an upward and downward direction to create a blood flow inside the first and second heart pumps thereby removing any air trapped in the system. When the de-airing procedure is completed the surgeon disassembles the manual de-airing handles from the valve cylinder casings and instead assembles the pump actuation enclosing parts to operate the valve cylinder as described above. The surgeon will gradually close down the heart-lung machine to let the four-chambered total artificial heart circulate the blood instead of the diseased heart.

A further advantage with enclosing the first and second artificial heart pumps as well as the pump actuating means in a leak-free blood pump housing device as described herein is that all inlet channels to the artificial atriums as well as the outlet channels exiting the artificial ventricles are arranged on the outside of the blood pump housing. Thus, all artery grafts as described above are easily accessible without having to open the blood pump housing device.

Furthermore, the mechanical parts such as cogwheels and screws which tend to wear out with time, as well as batteries which have a limited life time may easily be accessed.

BRIEF DESCRIPTION OF THE DRAWINGS

FIG. 3 is an exploded view of the blood pump housing device including artificial heart pumps and pump actuating means.

FIG. 4a is a detailed view of the valve cylinder and 4b is a view of the pump receiving parts FIG. 5 is cross sectional view of an artificial heart pump of the total artificial heart when fitted in a blood pumping device as described herein.

FIG. 6 is a cross sectional view of the two artificial heart pumps of a Total Artificial Heart.

FIG. 6a is a detailed view of the turning bend and the blood flow inside an artificial ventricle.

FIG. 14a is a detailed view of the pump actuating means according to a second embodiment and b is a view of pump actuating means according to a second embodiment when interacting with the valve cylinders.

DETAILED DESCRIPTION

In the following detailed description, reference is made to the accompanying set of drawings that form a part of the description hereof and in which several specific embodiments are shown by way of illustration. It is to be understood that other embodiments are contemplated and may be made without departing from the scope or spirit of the present invention. The following detailed description, therefore, is not to be taken in a limiting sense.

Figure 1:
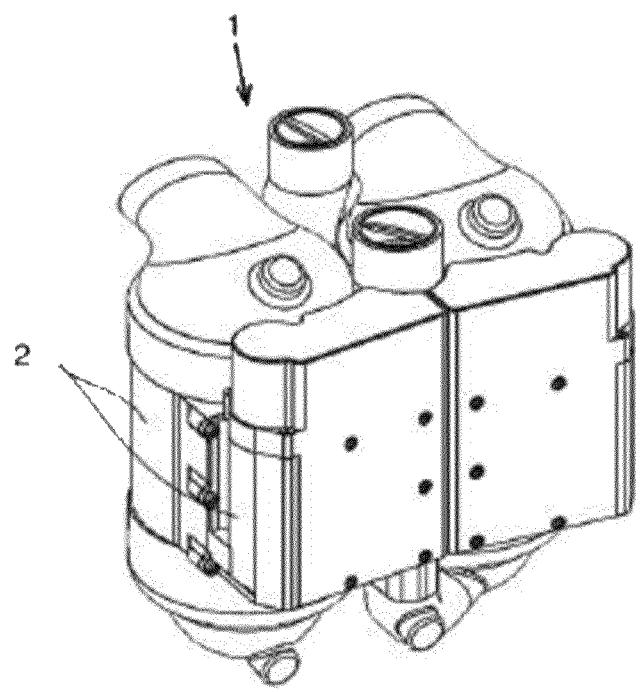
FIG. 1 is a view of the total artificial heart when arranged in the blood pump housing device.
Figure 2:
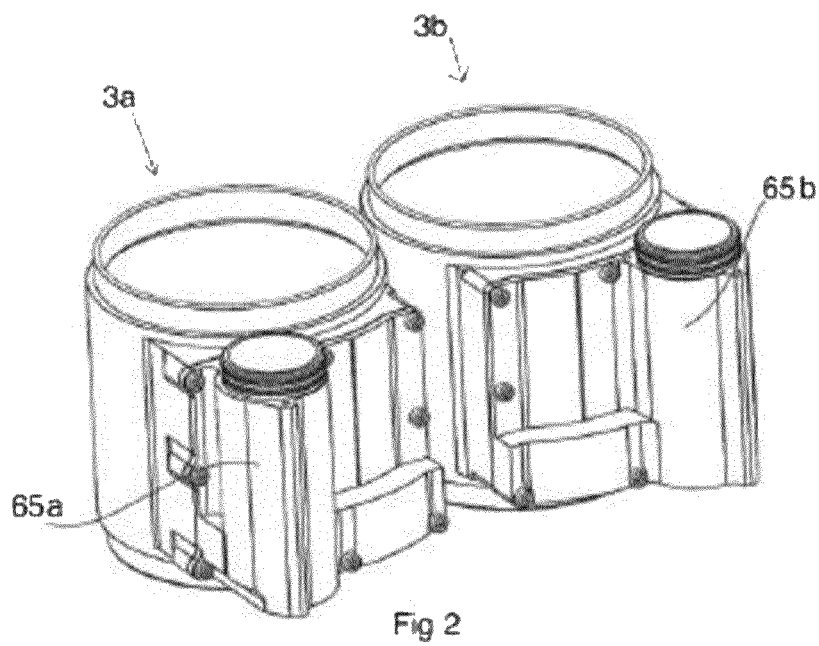
FIG. 2 is a view of the pump receiving parts when connected to the pump actuation casings.

The terms "a", "an", and "the" include plural referents unless the content clearly dictates otherwise. The term "or" is generally employed in its sense including "and/or" unless the content clearly dictates otherwise The total artificial heart 1 as described herein comprises a first and a second artificial heart pump 20a, 20b and first and second pump actuation means 60a, 60b enclosed in a blood pump housing device 2 (see FIGS. 1-3). The first and second artificial heart pumps 20a, 20b are identical and correspond to the left and right side of a natural heart. Hereinafter reference numbers denoting "a" refers to elements forming parts of the first artificial heart pump 20a and elements referred to as "b" form parts of the second artificial heart pump 20b. For instance the first pump actuation means 60a, actuates movement of the first artificial heart pump 20a, and the second pump actuation means 60b actuates movement of the second artificial heart pumps 20b to induce a blood flow in a body's vascular system.

The blood pump housing device 2 comprises two artificial heart pump receiving parts 3a, 3b and two pump actuation enclosing parts 4a, 4b (FIG. 3) connected together by connecting means 61a, 61b. Each artificial heart pump receiving part 3a, 3b encloses an artificial heart pump 20a, 20b and each pump actuation enclosing part 4a, 4b at least partly encloses the first and a pump actuating means 60a, 60b The first and second pump actuation means 60a, 60b actuate movement of the first and a second artificial heart pumps 20a, 20b to induce a blood flow in a body's vascular system. The first and second artificial heart pumps 20a, 20b are identical and correspond to the left and right side of a natural heart.

Each artificial heart pump receiving part 3a, 3b encloses a valve cylinder 22a, 22b (FIG. 4a) movably arranged inside said pump receiving part 3a, 3b (FIG. 4b). In the FIGS. 3, 5 and 6) the pump receiving parts 3a, 3b are shown either connected or separated from each other. Each pump receiving part 3a, 3b has an upper open end 6a, 6b and a lower open end 7a, 7b (see FIG. 4a). Each pump receiving part 3a, 3b is also provided with a pump actuation docking aperture 8a, 8b.

The upper open ends 6a, 6b of the pump receiving parts 3a, 3b are fitted with upper covers 23a, 23b provided with inlet channels 24a, 24b. The upper covers 23a, 23b together with the upper parts of the valve cylinders 22a and 22b form artificial atriums 25a, 25b corresponding to the atriums of the natural heart (see FIGS. 5 and 6).

The lower open ends 7a, 7b of the pump receiving parts 3a, 3b are fitted with lower covers 26a, 26b provided with outlet channels 27a, 27b, which together with the lower parts of the valve cylinders 22a, 22b form artificial ventricles 28a, 28b corresponding to the ventricles of the natural heart. The outlet channels 27a, 27b are provided with one-way valves 29a, 29b to ensure a unidirectional flow of blood through the artificial heart pumps 20a, 20b(FIGS. 5 and 6).

The artificial atriums 25a, 25b and ventricles 28a, 28b are separated by valve planes 31a, 31b, which are housed inside the valve cylinders 22a, 22b. The valve planes 31a, 31b are provided with valves 32a, 32b and arranged in the valve cylinders 22a, 22b, such that the valve planes 31a, 31b divide the valve cylinders 22a, 22b into two parts, one upper part and one lower part (FIGS. 5 and 6).

The upper and lower covers 23a, 23b and 26a, 26b are arranged in a leak-free manner onto the upper and lower open ends 6a, 6b and 7a, 7b respectively of the pump receiving part 3a, 3b. Advantageously the upper and lower covers 23a, 23b and 26a, 26b are glued to the upper and lower open ends 6a, 6b and 7a, 7b. Alternatively a gasket (not shown) made from a biocompatible rubber or silicon material is arranged between the covers and the upper and lower open ends 6a, 6b and 7a, 7b of the pump receiving parts 3a, 3b.

The first and second artificial heart pumps 20a, 20b are identical and the valves 32a, 32b provided in the valve cylinders 22a, 22b of each artificial heart pump 20a, 20b, correspond to the mitral valve 32a on the left side of the natural heart and the tricuspid valve 32b on the right side (FIGS. 5 and 6).

Pump actuating means 60a, 60b, are configured to apply a movement to said valve cylinders 22a, 22b in an upward and downward direction in response to control signals from a control unit (not shown) such that when the valve cylinders 22a, 22b move in an upward direction inside the blood pump housing device 2 (see FIG. 7a), the valves 32a, 32b provided in the valve planes 31a, 31b are in an open position allowing a flow of blood from the artificial atrium 25a, 25b to the artificial ventricle 28a, 28b, and when the valve cylinders 22a, 22b move in a downward direction (see FIG. 7b) the valves 32a, 32b are in the closed position and blood is ejected from the artificial ventricles 28a, 28b through the outlet channels 27a, 27b.

The internal structure of a natural ventricle has a sharp turn at the bottom of the ventricle i.e. at the apex of a natural heart, which forms a bend of approximately 110-150°. This means that when blood reaches the bottom of the apex it hits a stopping surface and most of the kinetic energy stored in the flowing blood which has flooded into the ventricle from the atrium through the open valve, is for a short moment transmitted to the heart muscle and thereafter transmitted back to the blood when the AV plane moves downward and pushes the blood from the ventricle. Next the blood leaves the heart through the aortic and pulmonary valves and continues into the aorta or the pulmonary arteries.

The stopping surface at the abrupt bend of the apex inside the ventricle makes the heart use less energy than expected considering that it has to pump a large volume of blood throughout the entire circulatory system. The repeated deceleration and acceleration of the moving blood inside the ventricles creates a dynamic flow of blood preventing the formation of blood clots.

Figure 8A:
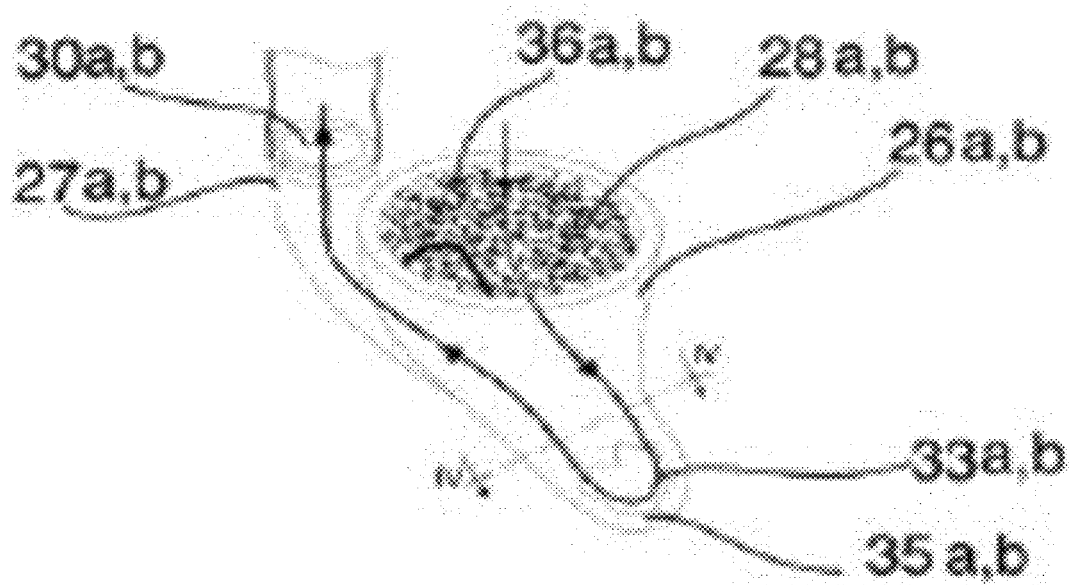
FIG. 8a is a detailed view of the turning bend and the blood flow inside an artificial ventricle.
Figure 8B:
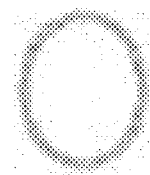
FIGS. 8b-8e are views of different cross-sectional shapes of the sharp bend inside the artificial ventricle.
Figure 8C:
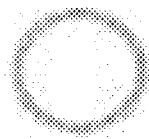

The artificial ventricles 28a, 28b of the four-chambered total artificial heart 1 as described herein comprise a turning portion 33a, 33b which mimics the design of the apex of a natural heart (see FIG. 8a). At the bottom of the artificial ventricles 28a, 28b i.e. at the bottom of the lower covers 26a, 26b the blood flow comes to a sudden stop and changes direction abruptly. The turn at the inside of the turning portion 33a, 33b at the bottom of the lower cover 26a, 26b forms a sharp bend of approximately 90-340°, more preferably between 100-300°, more preferably between 105-200°, and most preferably a bend between 110-150°, which is similar to the bend inside the ventricle of a natural heart. Thereafter the blood continues into the outlet channels 27a, 27b passes through the outlet valves 30a, 30b and subsequently into the major arteries. The cross section of the sharp turn 33a, 33b inside the artificial lower cover 26a, 26b advantageously has a bi-channeled shape 34a, 34b (see FIG. 8e). When used herein the term "bi-channeled shape" comprises a cavity cross-section which is oval with a waist to create two channels in the cavity of the ventricle. The bi-channeled shape enables an optimal flow of the blood through the artificial ventricle 28a, 28b.

Similar to a natural heart, a bi-channeled cross-section 34a, 34b of the turning portion 33a, 33b in the lower cover 26a, 26b facilitates the formation of several channels inside the cavity of the artificial ventricle to allow the blood to hit a stopping surface 35a, 35b at the bottom part of the turning portion 33a, 33b in the lower cover 26a, 26b before it changes direction and exits through the outlet channels 27a, 27. FIG. 8a illustrates how the blood enters the lower part of the lower cover 26a, 26b in the artificial ventricle 28a, 28b, hits the stopping surface 35a, 35b and exits the ventricle 28a, 28b through the outlet channel 27a, 27b and outlet valve 30a, 30b.

Figure 8D:
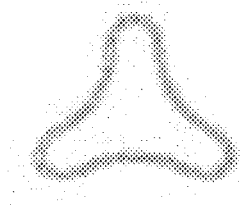
Figure 8E:
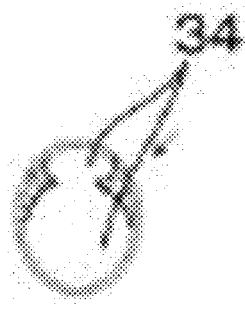
Figure 9:
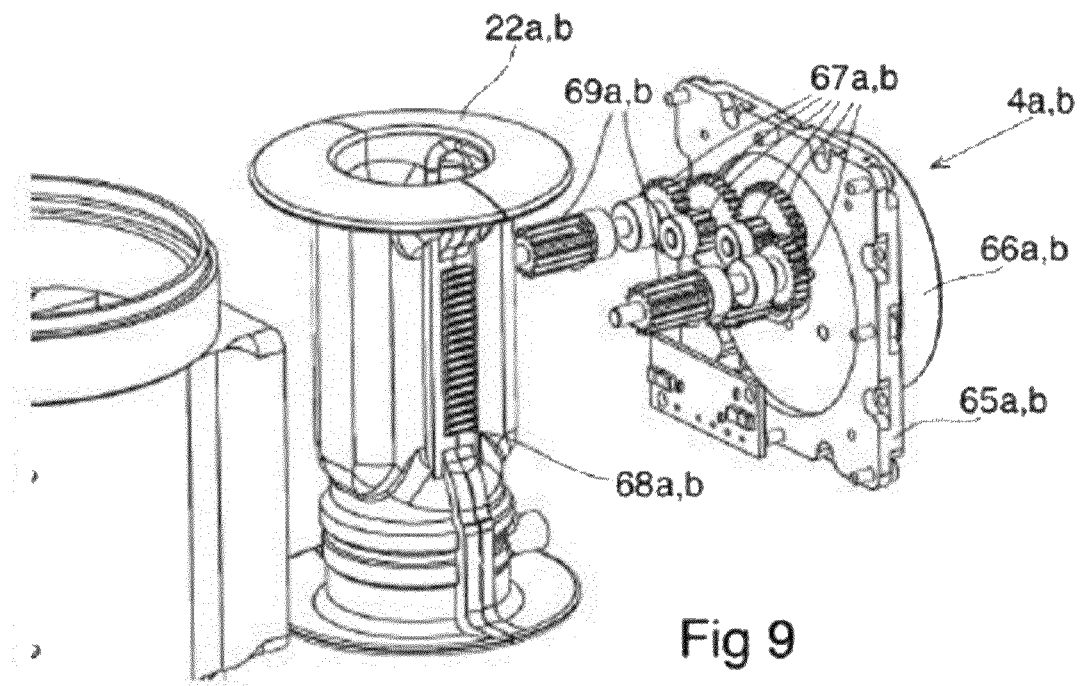
FIG. 9 is a perspective view of a first embodiment of the pump actuation means.
Figure 10:
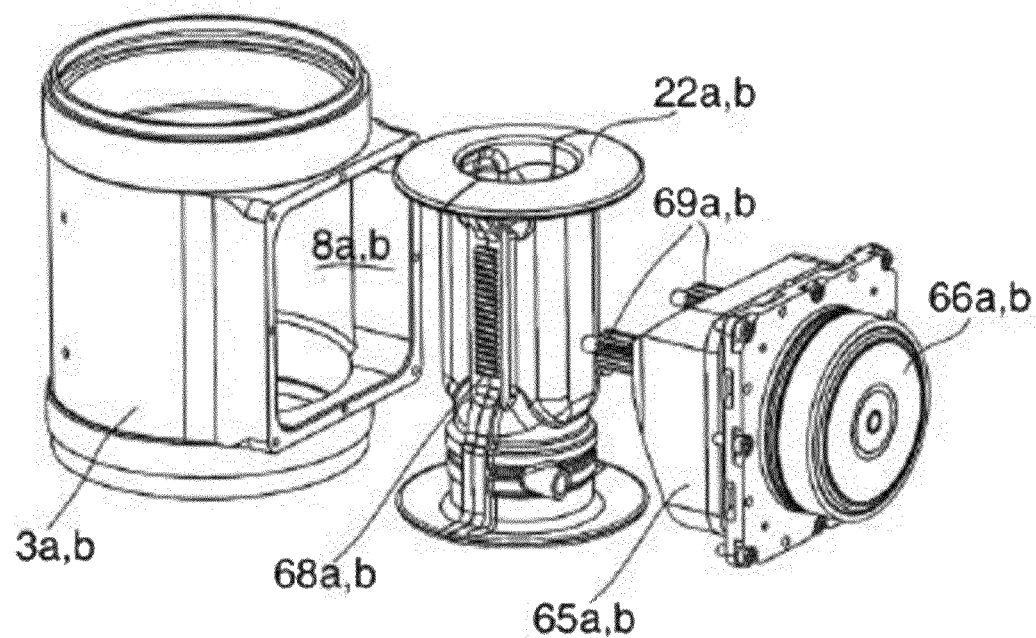
FIG. 10 is a view of the pump actuation means, the valve cylinder and the pump receiving part.
Figure 11:
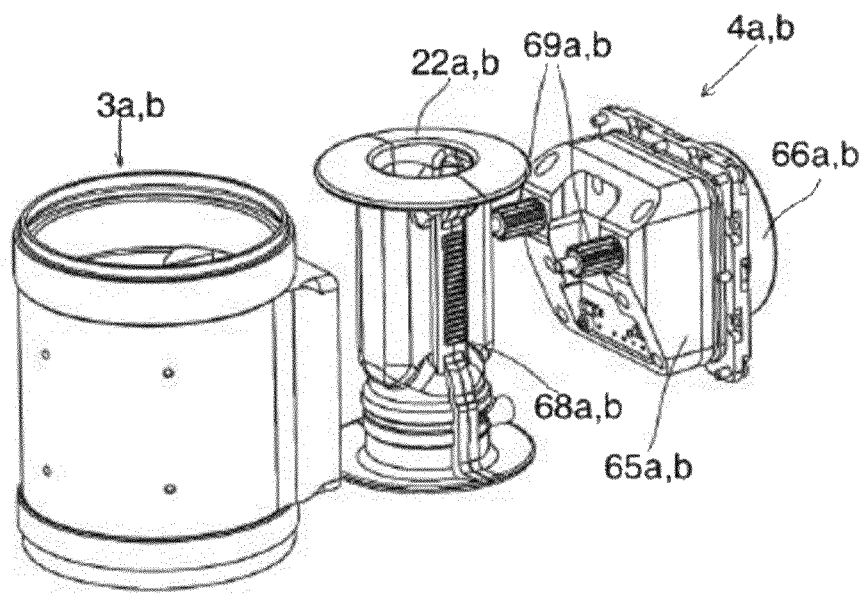
FIG. 11 is a view of the pump actuation means, the valve cylinder and the pump receiving part.
Figure 12:
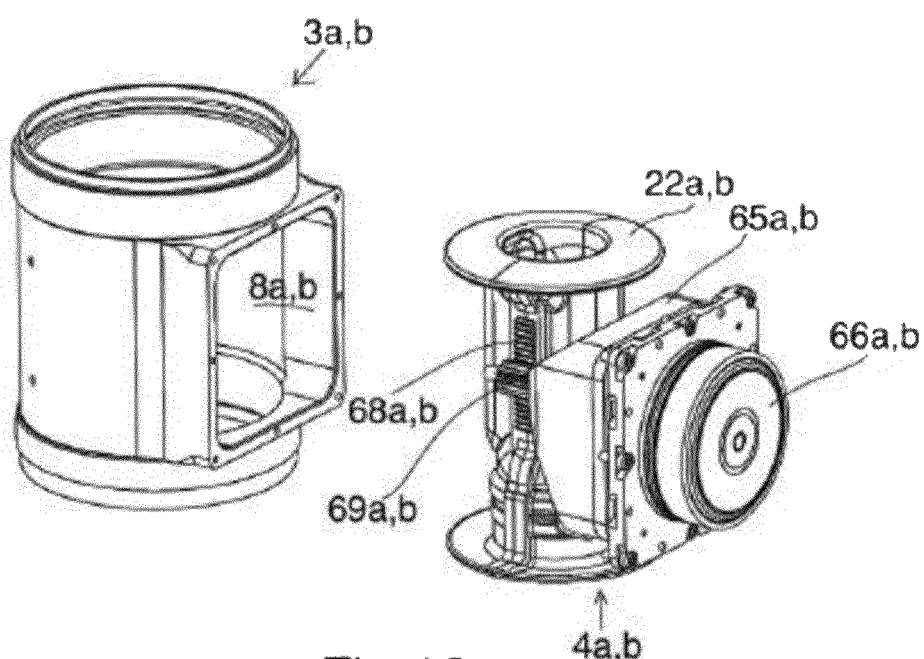
FIG. 12 is a view of the first embodiment of the interaction between the pump actuation means and the valve cylinder.
Figure 13:
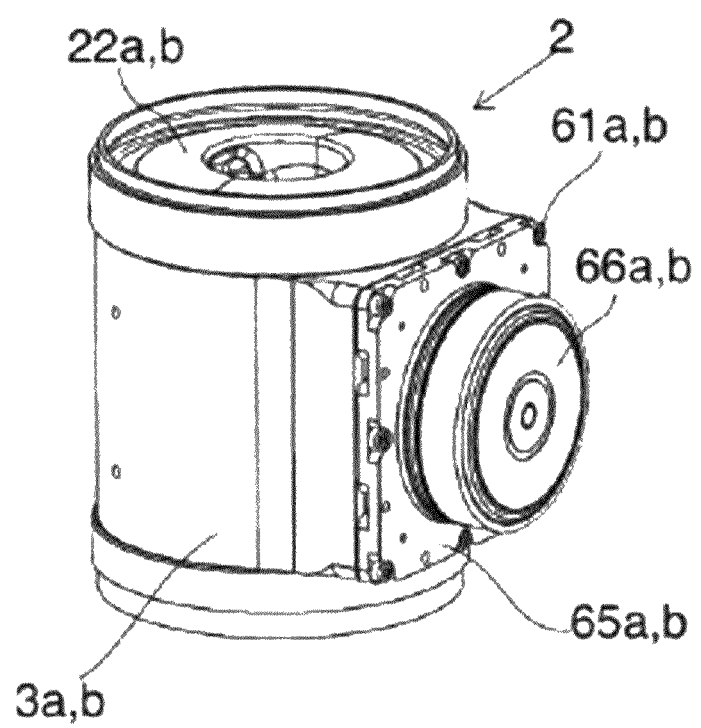
FIG. 13 is a view of the pump actuation means according to a first embodiment when docked to the pump receiving parts

The formation of channels inside the artificial ventricle may also prevent different blood flows from colliding with each other. FIGS. 8b-8e show views of the different cross sections the turning portion 33 a, 33 b may have to facilitate the flow towards the stopping surface 35 a, 35 b. FIG. 8d discloses a triangular shape, FIG. 8b, discloses an oval shape, FIG. 8e discloses an oval shape with a waist and FIG. 8 c is discloses a circular shape. The cross-sections of the turning portion 33 a, 33 b of the lower cover 26 a, 26 b may also have triangular, an oval shape 34 without a waist or a circular shape (see FIGS. 8b-8e).

The inner walls of the artificial ventricles 28a, 28b as well as the outlet channels 27a, 27b are advantageously provided with rough surfaces 36a, 36b to simulate the trabeculae carneae, i.e. the muscular ridges that crisscross and project from the inner walls of the ventricles of a natural heart.

A rough surface 36a, 36b minimizes the formation of eddies in the blood flow next to the wall of the artificial ventricle 28a, 28b much like when water flows past an obstacle in a river. With a flat ventricle wall the moving blood creates multiple swirls of blood close to the wall surface. Such blood swirls run opposite to the main blood stream disrupting the flow and decreasing the speed of blood inside the ventricle. A rough surface on the inside of the ventricles 28a, 28b and outlet channels 27a, 27 therefore minimizes the formation of blood swirls and further increases the speed of blood inside the artificial ventricle 28a, 28b of the four-chambered blood pumping device 1.

The outlet of the ventricle in a natural heart has a diameter which decreases continuously towards the aorta or the pulmonary arteries. Advantageously, the outlet channels 27a, 27b from the artificial ventricles 28a, 28b which are located in the lower covers 26a, 26b, also have a diameter which decreases continuously similarly to the design of the outlet of a ventricle in a natural heart. A rough inner surface 36a, 36b (FIG. 8a) together with a decreasing diameter of the outlet channel 27a, 27b will significantly increase the speed of the blood flow exiting the artificial ventricles 28a, 28b of the four-chambered total artificial heart 1.

The artificial heart pump receiving parts 3a, 3b and pump actuation enclosing parts 4a, 4b of the blood pump housing device 2 are advantageously made from a stiff material, such as e.g. a biocompatible material such as, titanium, ceramics, Polytetrafluoroethylene (PTFE) coated metal, diamond coated metal, silicone or polyurethane coated metals or a combination thereof.

Figure 7A:
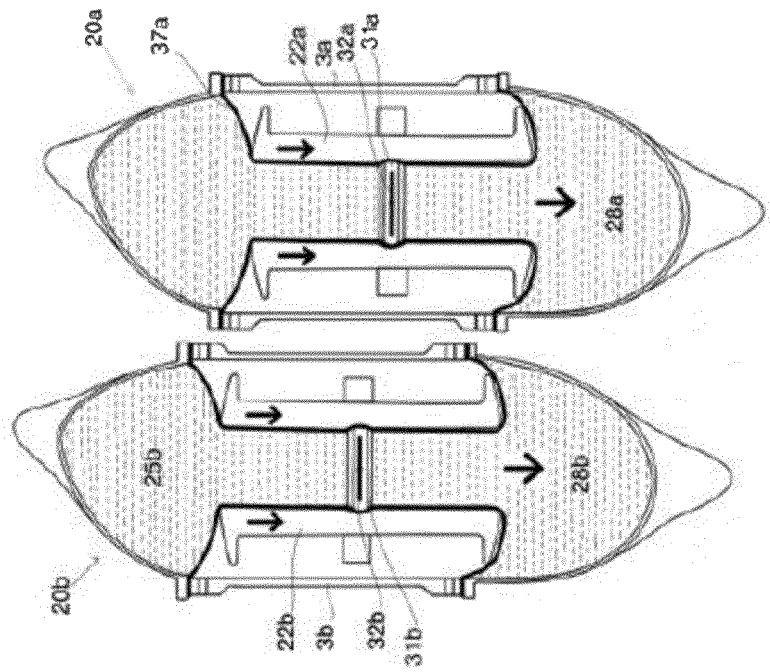
FIGS. 7a and b are views of the blood flow through the artificial heart during diastole (7a) and systole (7b).
Figure 7B:
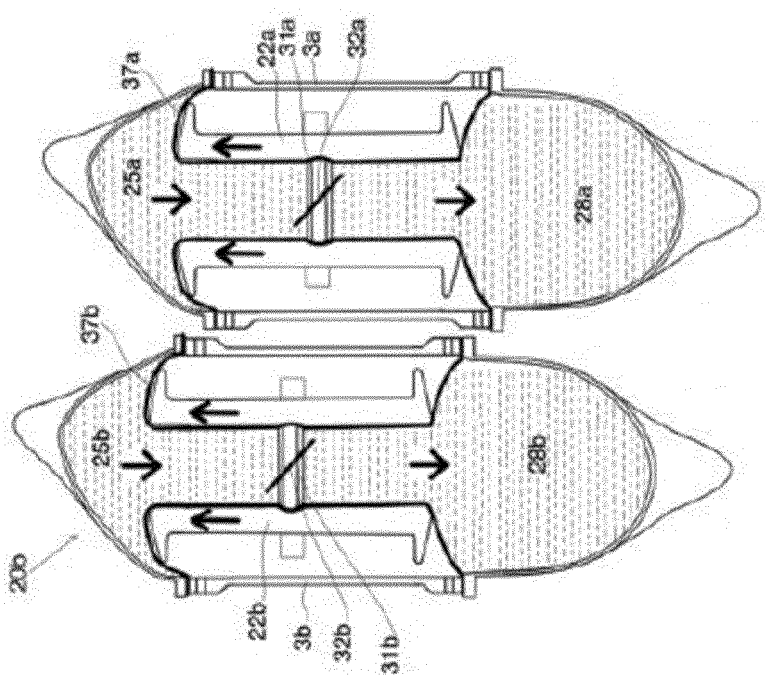

The insides of the artificial atriums 25a, 25b and ventricles 28a, 28b are provided with a flexible lining material 37a, 37b to prevent blood from leaking from the artificial heart pump (see FIGS. 7a and 7b). The flexible lining material 37a, 37b may also be comprised of two or more layers of material to improve its strength. The flexible lining material 37a, 37b is advantageously made from a biocompatible material like silicone, polyurethane or another biocompatible material.

Inside the artificial atrium 25a, 25b the flexible lining material 37a, 37b is connected to upper cylinder junctions between the upper covers 23a, 23b and the top edge of the valve cylinder casing upper open ends 6a, 6b to prevent any leakage through said upper cylinder junctions.

Inside the artificial ventricles 28a, 28b the flexible lining material 37a, 37b is also connected to the lower cylinder junctions between the lower covers 26a, 26b and the bottom edge of the valve cylinder casing lower open end 7a, 7b to prevent any leakage through the lower cylinder junctions. The flexible lining material 37a, 37b is fixed to the upper and lower cylinder junctions e.g. by means of biocompatible glue or alternatively by screws.

As seen in FIGS. 5, 6 and 7a and 7b by means of the flexible lining a leak-free pipeline is formed in the artificial heart through which blood is pumped in a continuous pulsating flow from the entrance of the inlet channel 24a, 24b through the artificial atrium 25a, 25b, the valve 32a, 32b, the ventricle 28a, 28b and out through the outlet channel 27a, 27b.

The outlet channels 27a, 27b of the four-chambered total artificial heart are provided with one-way outlet valves 30a, 30b to prevent the return of blood back into the artificial ventricles 28 after the blood has been ejected through the outlet channels 27a, 27b. The one-way outlet channel valves 30a, 30b correspond to the aortic valve 30a or the pulmonary valve 30b respectively of the natural heart.

The first and second pump actuating means 60a, 60b are configured to apply movement to said valve cylinders 22a, 22b in an upward and downward direction in response to control signals from a control unit. The first and second pump actuating means 60a, 60b are each at least partly housed by a pump actuation casing 65a, 65b which form part of pump actuation enclosing part 4a, 4b (see FIG. 3). Advantageously the two pump actuation casings 65a, 65b are connected together. Each of the first and second pump actuation casings 65a, 65b are configured to receive and enclose a pump actuating means 60a, 60b and dock to docking apertures 8a, 8b provided on the pump receiving parts 3a, 3b.

When said first and second pump actuation casings 65a, 65b are docked to said docking apertures 8a, 8b on the pump receiving parts 3a, 3b, said first and second pump actuating means 60a, 60b are configured to apply movement to the valve cylinders 22a, 22b in an upward and downward movement in response to control signals from a control unit.

The term "dock to" when used herein is intended to mean that the pump actuation casings 65a, 65b are configured to connect to the apertures 8a, 8b provided on the pump receiving parts 3a, 3b. The pump actuation casings 65a, 65b dock to the pump receiving parts 3a, 3b in a leek free manner to prevent body fluids from entering the blood pump housing device 2.

The pump actuation casings 65a, 65b are docked to the docking apertures 8a, 8b by means of connecting means 61a, 61b selected from the group consisting of glue, connecting screws, bolts and nuts, clamps and/or clips. Advantageously first and second pump actuation casings 65a, 65b are connected to the docking apertures 8a, 8b in a reversible manner such that the pump actuation enclosing parts 3a, 3b are easily removed if the artificial heart pumps 20a, 20b or pump actuation means 60a, 60b require maintenance. Advantageously a gasket is provided in the connection between the first and second pump actuation casings 65a, 65b and the docking apertures 8a, 8b of the pump receiving parts 3a, 3b.

The upward and downward motion of the valve cylinders 22a, 22b may be achieved in many different ways. In one advantageous embodiment as seen in FIGS. 9-13, the pump actuation means 60a, 60b actuates rotation of a plurality of gears 67a, 67b (see FIG. 9) of different sizes configured to interact with one another and a pinion 69a, 69b to translate a rotational movement into a first and second linear toothed means 68a, 68b provided on each side of the valve cylinder 22a, 22b. When the pump actuation means rotates the gears 67 in a first rotational direction, teeth provided on the pinion 69a, 69b interact with teeth on the linear toothed means 68a, 68b on the valve cylinder 22a, 22b and moves said valve cylinder 22a, 22b in a first linear direction.

Thereafter the pump actuation means changes direction into a second rotational direction opposite to said first rotational direction and moves said valve cylinder 22a, 22b in a second linear direction opposite to said first linear direction. The rotational speed and length of rotational movement is adjusted to provide appropriate speed and length of the up-and-down movement of the valve cylinders 22a, 22b to induce correct blood flow through the TAH 1 and into the vascular system.

In an alternative embodiment as seen in FIGS. 14a, 14b, the pump actuating means 60a, 60b comprises a ball screw or a roller screw 62 which translates a rotational motion into a linear up-and-down motion of the valve cylinders 22a, 22b. The ball screw or roller screw gear-box 62a, 62b translates a rotational motion provided by a pump actuation means into a linear up-and-down motion of the valve cylinders 22a, 22b inside the pump receiving parts 3a, 3b. The nut of the ball or roller screw 62a, 62b is an integrated part of the pump actuating assembly and forms the base from which two arms 63a, 63b of the pump actuating means 60a, 60b extend around at least part of the valve cylinder 22a, 22b circumference and connect thereto. The screw of the ball or roller screw 62a, 62b is provided with a first cogwheel 71a, 71b in a cooperative arrangement with a second cogwheel 72a, 72b with different diameter to form a gearbox, which in turn is connected to a motor cogwheel 73a, 73b of a pump actuation means, such as e.g. an electromechanical motor.

When the pump actuation means rotates the motor cogwheel 73a, 73b, said motor cogwheel cooperates with the gearbox cogwheel 71a, 71b and with a cogwheel 72a, 72b provided on the screw of the ball or roller screw 62a, 62b rotating said screw. When the ball or roller screw 62a, 62b rotates, its rotational movement is translated into a linear movement of the first and second pump actuation means 60a, 60b i.e. the nut with the arms 63a, 63b which moves the valve cylinder 22a, 22b in an upward direction or a downward direction depending on the direction of rotation of the electromechanical motor. Each valve cylinder 22a, 22b is provided with two or more cylinder magnets 40a, 40b arranged to interact with actuation magnets 64a, 64b provided on the arms 63a, 63b. Each artificial heart pump 20a, 20b contains a pump actuating means 60a, 60b and both artificial heart pumps 20a, 20b of the heart operate simultaneously and in the same direction (FIGS. 14a and 14b).

The energy to power the pump actuating means 60a, 60b may be supplied by an external source via a cable through the skin, or alternatively by an implanted battery. The implanted battery may be recharged from the outside via a cable or by means of induction or ultra sound.

Micro-computer or electronic chips configured to receive signals from pressure sensors may be arranged around major arteries or alternatively be integrated inside the cavity or the walls of the artificial atriums or ventricles or both. When the patient changes his physical activities the blood pressure will reflect the situation. Alternatively the micro-computer or electronic chips may also receive signals from an oxygen sector sensor arranged around major or minor arteries or alternatively integrated inside blood vessels. However, the micro-computer or electronic chips may also receive signals from thermal sensors arranged around major arteries, integrated inside vessels or alternatively integrated anywhere in the chest cavity. The body temperature, which increases with physical activity, may also be used to activate the pump actuating means during high physical efforts. The micro-computer or electronic chips may also receive signals from positional sensors arranged inside the four-chambered total artificial heart to reflect whether the patient is standing or lying down.

The micro-computer or the electronic chips will send information to the pump actuating means to change its pumping activity accordingly. If for some reason the micro-computer or electronic chips are not receiving any input information, the pump actuating means will continue at a constant level of activity, and instead the patient will have to adjust his physical activities.

The micro-computer or the electronic chips will advantageously be designed to send information and have the capability to communicate with a communicator such as a pocket device carried by the patient or to as an application in the patients smart mobile device. Advantageously the communicator may also send an alarm if something wrong occurred to the four-chambered total artificial heart, or reflect the status during use, the temperature of the electrical motor or when the pressure inside the Artificial atrium or ventricle exceed an upper limit.

Figure 15:
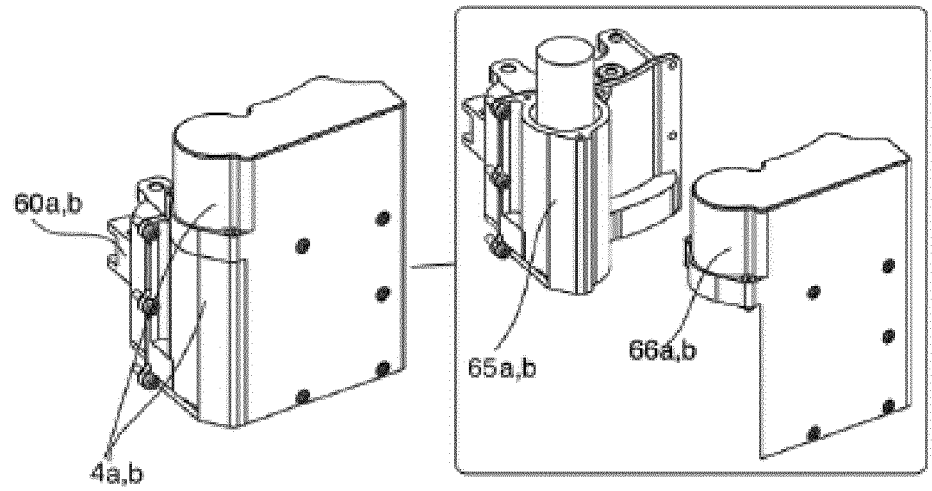
FIG. 15 is an exploded view of the pump actuation casing fitted with a detachable power storage casing.

In an advantageous embodiment the pump actuation enclosing parts 4a, 4b may comprise a separate and detachable power source casing 66a, 66b (see FIG. 15) configured to store any power source used to power the pump actuation means 60a, 60b such as rechargeable batteries. The power source casings 66a, 66b may also house any micro-computers and/or electronic chips used to receive signals from sensors in the artificial four-chambered heart or to control the pump actuation means 60a, 60b.

Figure 16:
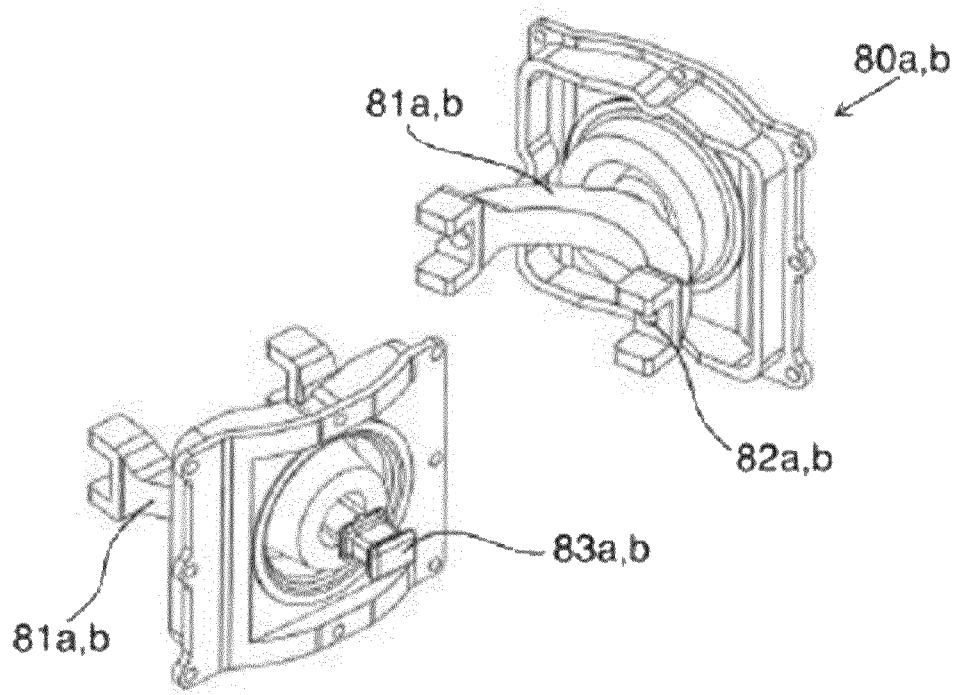
FIG. 16 is a view of the pump de-airing handle.

In order to evacuate the four-chambered artificial heart 1 from air before starting the blood flow a pump de-airing handle 80 (see FIG. 16) may be assembled onto the docking apertures 8a, 8b in a leek free manner instead of pump actuation casings 65a, 65b. Two de-airing arms 81 of the pump de-airing handle 80 extend around at least part of the valve cylinder 22a, 22b circumference and connect thereto.

Each arm of the pump de-airing handle 80 is provided with two or more magnets 82 arranged to interact with the cylinder magnets 40 provided on the valve cylinders 22a, 22b. Thus the pump de-airing handle 80 manually operate the artificial heart pump 20a, 20 during the implantation procedure.

The invention claimed is:

1. A blood pump system comprising:
    a total artificial heart (TAH) comprising:
        first and second artificial heart pumps; and
        first and second pump actuation means that are each configured to actuate a respective one of the first and second artificial heart pumps; and
    a housing device comprising:
        first and second artificial heart pump receiving parts that are each configured to receive and partly enclose a respective one of the first and second artificial heart pumps; and
        first and second pump actuation means enclosing parts that are each configured to partly enclose a respective one of the first and second pump actuation means, wherein said first and second artificial heart pump receiving parts and respective pump actuation means enclosing parts of the first and second pump actuation means enclosing parts are arranged to connect to each other in a leak-free manner;
    characterized in that each artificial heart pump of said first and second artificial heart pumps comprises a valve cylinder movably arranged inside said respective one of said first and second artificial heart pump receiving parts, wherein said cylinder has a valve plane provided with a valve, said valve plane dividing said valve cylinder into an artificial atrium and an artificial ventricle,
    wherein each pump receiving part of the first and second artificial heart pump receiving parts has an upper open end and a lower open end, said upper open end is arranged with an upper cover provided with an inlet channel, and said lower open end is arranged with a lower cover provided with an outlet channel, and
    wherein said artificial atriums and ventricles of said first and second artificial heart pumps are provided with a flexible lining material, and wherein said flexible lining material is connected to an upper cylinder junction arranged between said upper cover and a top edge of said upper open end, and to a lower cylinder junction arranged between said lower cover and a bottom edge of said lower open end.

2. The blood pump system according to claim 1, wherein the first and second artificial heart pump receiving parts are connected to the first and second pump actuation means enclosing parts by connecting means selected from the group consisting of screws, ribbons, bolts, nuts, and glue.

3. The blood pump system according to claim 1, wherein the outlet channels are provided with one-way valves.

4. The blood pump system according claim 1, wherein the first and second pump receiving parts and the first and second pump actuation means enclosing parts are manufactured from a biocompatible material selected from the group consisting of titanium, ceramics, Polytetrafluoroethylene (PTFE) coated metal, diamond coated metal, silicone, and polyurethane coated metals, or a combination thereof.

5. A blood pump housing device comprising
    first and second artificial heart pump receiving parts that are each configured to receive and partly enclose a respective one of first and second artificial heart pumps of a total artificial heart (TAH); and
    first and second pump actuation means enclosing parts configured to partly enclose a respective one of first and second pump actuation means, wherein said first and second artificial heart pump receiving parts and respective pump actuation means enclosing parts of the first and second pump actuation means enclosing parts are arranged to connect to each other in a leak-free manner;
    characterized in that each artificial heart pump of said first and second artificial heart pumps comprises a valve cylinder movably arranged inside said respective one of said first and second artificial heart pump receiving parts, wherein said cylinder has a valve plane provided with a valve,
    wherein said valve cylinder is separated by the valve plane, said valve plane dividing said valve cylinder into an artificial atrium and an artificial ventricle,
    wherein each pump receiving part of the first and second artificial heart pump receiving parts has an upper open end and a lower open end, said upper open end is arranged with an upper cover provided with an inlet channel, and said lower open end is arranged with a lower cover provided with an outlet channel, and
    wherein said artificial atriums and ventricles of said first and second artificial heart pumps are provided with a flexible lining material, and wherein said flexible lining material is connected to an upper cylinder junction arranged between said upper cover and a top edge of said upper open end, and to a lower cylinder junction arranged between said lower cover and a bottom edge of the lower open end.

6. The blood pump system according to claim 1, wherein said first and second pump receiving parts comprise respective docking apertures.

7. The blood pump system according to claim 6, wherein each of the first and second pump actuation means enclosing parts comprises a pump actuation casing, and wherein each pump actuation casing of the first and second pump actuation means enclosing parts is configured to receive and enclose a respective one of the first and second pump actuation means and dock to the respective docking aperture on the first and second pump receiving parts.

8. The blood pump system according to claim 7, wherein when said first and second pump actuation casings are docked to said respective docking apertures of said first and second pump receiving parts said first and second pump actuation means are configured to apply movement to the valve cylinders in an upward and downward movement in response to control signals from a control unit.

9. The blood pump system according to claim 7, wherein said pump actuation casings of the first and second pump actuation means enclosing parts are docked to said docking apertures of the pump receiving parts by means of connecting means selected from the group consisting of glue, connecting screws, bolts and nuts, clamps, and clips.

10. The blood pump system according to claim 9, wherein the connecting means are bolts and nuts.

11. A blood pump housing device comprising
    first and second artificial heart pump receiving parts configured to receive and partly enclose a respective one of first and second artificial heart pumps of a total artificial heart (TAH); and
    first and second pump actuation means enclosing parts configured to partly enclose a respective one of first and second pump actuation means, wherein said first and second artificial heart pump receiving parts and respective pump actuation means enclosing parts of the first and second pump actuation means enclosing parts are arranged to connect to each other in a leak-free manner;

characterized in that each artificial heart pump of said first and second artificial heart pumps comprises a valve cylinder movably arranged inside said respective one of said first and second artificial heart pump receiving parts, wherein said cylinder has a valve plane provided with a valve, wherein the pump actuation means comprises a plurality of interconnected gears configured to interact with first and second linear toothed means provided respectively on each side of the valve cylinder, wherein said gears translate a rotational movement provided by the pump actuation means to a linear up-and-down movement of the valve cylinder.

12. The blood pump system according to claim 1, wherein the pump actuating means comprises a ball screw/roller screw interconnected with a semicircular base comprising two projecting arms which partly encircle and connect to said valve cylinders of said first and second artificial heart pumps, wherein said ball screw/roller screw is interconnected to a plurality of gears which translates a rotational motion provided by the pump actuation means, into a linear up-and-down motion of the valve cylinders.

13. The blood pump system according to claim 12, wherein actuation magnets provided on said two projecting arms are connected to cylinder magnets provided on said valve cylinders.

14. The blood pump system according to claim 1, wherein the pump actuation means enclosing part comprises a detachable power source housing.

15. The blood pump system according to claim 1, wherein the first and the second pump actuation means enclosing parts fully enclose, respectively, the first and second pump actuation means.

16. The blood pump system of claim 1, wherein the pump actuation means comprises a plurality of interconnected gears configured to interact with first and second linear toothed means provided respectively on each side of the valve cylinder, wherein said gears translate a rotational movement provided by the pump actuation means to a linear up-and-down movement of the valve cylinder.

* * * * *